United States Patent [19]

Miyashita et al.

[11] 4,309,428
[45] Jan. 5, 1982

[54] MAYTANSINOIDS

[75] Inventors: Osamu Miyashita, Osaka; Hiroshi Akimoto, Nishinomiya, both of Japan

[73] Assignee: Takeda Chemical Industries, Ltd., Tokyo, Japan

[21] Appl. No.: 171,459

[22] Filed: Jul. 23, 1980

[30] Foreign Application Priority Data

Jul. 30, 1979 [JP] Japan .................................. 54-97779
Jun. 9, 1980 [JP] Japan .................................. 55-78142

[51] Int. Cl.³ .................. A61K 31/535; C07D 498/16
[52] U.S. Cl. .......................... 424/248.54; 260/239.3 P
[58] Field of Search ................. 260/239.3 P; 424/248.54

[56] References Cited

PUBLICATIONS

Noller "Chemistry of Organic Compounds", 2nd Edition, (Saunders) (1957), p. 504.
Kupchan et al. "Journal of Medicinal Chemistry", vol. 21, No. 1, (1978), pp. 31–37.

Primary Examiner—Robert T. Bond
Attorney, Agent, or Firm—Wegner & Bretschneider

[57] ABSTRACT

Novel maytansinoids of the formula:

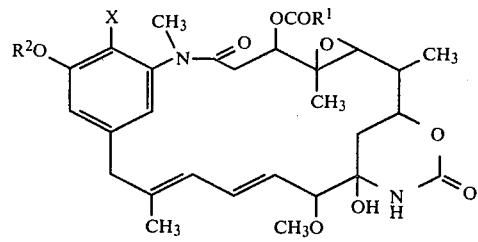

wherein
X is hydrogen or chlorine,
$R^1$ is $C_{2-4}$ alkyl,
$R^2$ is $C_{2-8}$ alkyl which may be substituted or methyl which is substituted,
have antimicrobial, antimitotic and antitumor activities.

12 Claims, No Drawings

MAYTANSINOIDS

This invention relates to novel maytansinoid compounds which are of value as medicines and to their production and use.

More particularly, this invention provides compounds of the formula:

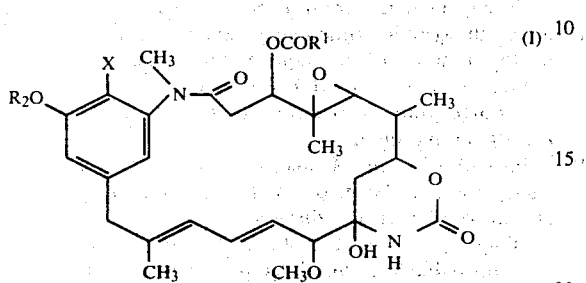

wherein X is hydrogen or chlorine; $R^1$ is $C_{2-4}$ alkyl; $R^2$ is $C_{2-8}$ alkyl which may be substituted or methyl which is substituted.

Referring to the above formula (I), the $C_{2-4}$ alkyl group $R^1$ is exemplified by ethyl, propyl, isopropyl, butyl, sec-butyl, tert-butyl, etc. Especially preferred is isopropyl.

The $C_{2-8}$ alkyl group $R^2$ is exemplified by ethyl, propyl, isopropyl, butyl, sec-butyl, pentyl, isopentyl, hexyl, heptyl, octyl, etc., and $C_{2-5}$ alkyl is preferred.

The substituents on the $C_{2-8}$ alkyl group and on the methyl group as $R^2$ are exemplified by halogen (e.g. chlorine, bromine, iodine), carboxyl, $C_{2-5}$ alkoxycarbonyl (e.g. methoxycarbonyl, ethoxycarbonyl, isopropoxycarbonyl, butoxycarbonyl, tert-butoxycarbonyl), phenoxycarbonyl, benzyloxycarbonyl, hydroxyl, $C_{1-4}$ alkoxy (e.g. methoxy, ethoxy, propoxy, isopropoxy, butoxy, isobutoxy, sec-butoxy, tertbutoxy, the terminal of which may be substituted with $C_{1-4}$ alkoxy or $-O-(CH_2CH_2O)_n-H[n$ is integer 1 to 5]), benzyloxy, $C_{1-4}$ alkylthio (e.g. methylthio, ethylthio, propylthi butylthio), benzylthio phenylthio, $C_{1-4}$ alkylsulfinyl (e.g. methylsulfinyl, ethylsulfinyl, propylsulfinyl, butylsulfinyl), benzylsulfinyl, phenylsulfinyl, $C_{1-4}$ alkylsulfonyl (e.g. methylsulfonyl, ethylsulfonyl, propylsulfonyl, butylsulfonyl), benzylsulfonyl, phenylsulfonyl, $C_{1-5}$ alkanoyloxy (e.g. formyloxy, acetyloxy, propionyloxy, butyryloxy, isobutyryloxy, valeryloxy, pivaloyloxy), benzoyloxy, phenylacetyloxy, cyano, dialkylamino, (e.g. dimethylamino, diethylamino, dibutylamino), oxo (which is not on α-carbon of $C_{2-8}$ alkyl or methyl and which may be acetalized by $C_{1-4}$ alcohol or diol, mercaptan or dimercaptol or iminated by hydrazine which may be substituted), $C_{1-4}$ 1-alkylidene (e.g. methylene, ethylidene, propylidene) which may be substituted with $C_{1-4}$ alkoxycarbonyl or cyano, phenyl, α- or β-naphthyl, vinyl, ethynyl, $C_{3-6}$ cycloalkyl (e.g. cyclopropyl, cyclobutyl, cyclopentyl, cyclohexyl), 5- or 6-membered N, O or/and S-containing heterocyclic groups (e.g. pyridyl, pyrimidyl, pyrazinyl, pyridazinyl, triazinyl, piperidinyl, piperazinyl, pyrrolyl, pyrrolidinyl, pyrrolinyl, imidazolyl, pyrazolyl, triazolyl, tetrazolyl, imidazolinyl, pyrazolidinyl, imidazolidinyl, triazolidinyl, furyl, furanyl, tetrahydrofuryl, thienyl, morpholino, oxazolyl, oxazolynyl, thiazolyl, thiazolinyl, oxadiazolyl, thiadiazolyl), oxylanyl, dioxolanyl, dithiolanyl, etc.

Each of the above-mentioned cyclic groups and vinyl and ethynyl groups may be further substituted. The substituents include, for example, $C_{1-4}$ alkyl (e.g. methyl, ethyl, propyl, isopropyl, butyl, isobutyl, sec-butyl, tert-butyl), hydroxyl, $C_{1-4}$ alkoxy (e.g. methoxy, ethoxy, propoxy, isopropoxy, butoxy, isobutoxy, sec-butoxy, tertbutoxy), $C_{1-4}$ alkanoyloxy (e.g. formyloxy, acetyloxy, propionyloxy, butyryloxy, isobutyryloxy), $C_{2-5}$ alkoxycarbonyl (e.g. methoxycarbonyl, ethoxycarbonyl, propoxycarbonyl, isopropoxycarbonyl, butoxycarbonyl, isobutoxycarbonyl, secbutoxycarbonyl, tert-butoxycarbonyl), halogen (e.g. chlorine, fluorine, bromine, iodine), nitro, cyano, trifluoromethyl, amino, mono-$C_{1-4}$ alkylamino (e.g. methylamino, ethylamino, propylamino, isopropylamino, butylamino, isobutylamino), di-$C_{1-4}$ alkylamino (e.g. dimethylamino, diethylamino, bis(2-chloroethyl)amino, dipropylamino, dibutylamino), $C_{1-4}$ alkylthio (e.g. methylthio, ethylthio, propylthio, isopropylthio, butylthio, isobutylthio, sec-butylthio, tert-butylthio), $C_{1-4}$ alkylsulfinyl (e.g. methylsulfinyl), $C_{1-4}$ alkanesulfonyl (e.g. methanesulfonyl), $C_{1-4}$ alkanoylamino (e.g. formylamino, acetylamino, propionylamino, butyrylamino, isobutyrylamino), sulfo, sulfamoyl (e.g. sulfamoyl, N-methylsulfamoyl, N,N-dimethylsulfamoyl), sulfonylamino (e.g. methanesulfonylamino, benzenesulfonylamino, p-toluenesulfonylamino), $C_{1-4}$ alkanoyl (e.g. acetyl, propionyl, vutyryl, isobutyryl), benzyloxy, benzylthio, benzyloxycarbonyloxy, tert-butoxycarbonyloxy, benzylamino, etc.

The compound (I) according to this invention can be produced for example by alkylating a 20-demethoxy-20-hydroxymaytansinol 3-lower carboxylate of the formula:

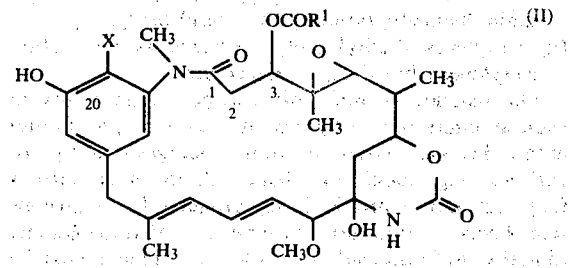

wherein X and $R^1$ are as previously defined.

The alkylation reaction is carried out by using an alkylating agent capable of introducing an alkyl group into the position of 20-hydroxyl group. The alkylating agent, which corresponds to $R^2$ to be introduced, includes, for example:

(a) diazoalkanes: diazomethane, diazoethane, α-diazotoluene, α-diazoacetophenone, ethyl diazoacetate, diethyl diazomalonate (b) trialkyloxonium salts: trimethyl oxonium fluoroborate, triethyloxonium fluoroborate (c) halides: methyl iodide, ethyl idodide, propyl bromide, isopropyl bromide, butyl bromide, pentyl bromide, hexyl bromide, heptyl bromide, octyl bromide, propyl chloride, butyl chloride, benzyl chloride, benzyl bromide, allyl chloride, allyl bromide, crotonyl bromide, propargyl bromide, bromoacetaldehyde diethyl acet 1, 3-chloropropionaldehyde diethyl acetal, chloroacetonitrile, 3-chloropropionitrile, chloroacetone, ethyl 4-chloroacetoacetate, 1,7-dibromo-2,6-heptanedione, 1-chloro-3-oxopentane, 1,5- dichloro-2-oxopentane, bromoacetone, α-bromoacetophenone, 2-, 3- or 4-chloro-α-bromoacetophenone, 2,6-dichloro-α-bromoacetophenone, 2-, 3- or 4-methyl-α-bromoacetophenone, 2-, 3- or 4-methoxy-α-bromoacetophenone, 2,5-dimethoxy-α-bromoacetophenone, α-chloro-4-fluoroacetophenone, 2- or 4-nitro-α-chloroacetophenone, 4-bromo-γ-bromobutyrophenone, ethyl chloroacetate, ethyl bromoacetate, ethyl 3-bromopropionate, ethyl bromomalonate, epichlorohydrin, epibromohydrin, ethyl bromocyanoacetate, ethyl γ-bromocrotonate, chloromethyl methyl ether, 2-bromoethyl ethyl ether, chloromethyl ethyl ether, benzyl chloromethyl ether, chloromethyl methyl sulfide, benzyl chloromethyl sulfide, chloromethylphenyl sulfide, chloromethyl acetate, chloromethyl pivalate, N-chloromethylmorpholine, furfuryl chloride, 5-nitrofurfuryl chloride, thenyl chloride, 2-, 3- or 4-picolyl chloride, 5-chloromethyl-2-oxazolidone, 5-chloromethyl-1,2,4-oxadiazole, 1,2-dimethyl-5-chloromethylimidazole, 5-methyl-5-chloromethylisoxazole, 5-methyl-2-chloromethylthiazole, 5-methylthio-2-chloromethyl-1,3,4-thiadiazole,, 1-methyl-5-chloromethyl-1,2,3-triazole, 1-methyl-5-chloromethyltetrazole, 2-chloromethylbenzimidazole, 2-chloromethylbenzo-1,4-dioxane, 5-fluoro-2-bromomethylcoumaran, α-chloromethylnapthalene, β-bromomethylnaphthelene (d) sulfates: dimethyl sulfate, diethyl sulfate, ethyl p-toluenesulfate, 2-(2-ethoxyethoxy)ethanol p-toluenesulfonate, hexaethylene glycol p-toluenesulfonate (e) Isoureas: O-methyl-, O-ethyl, O-isopropyl- or O-benzyl-N,N'-dicyclohexylisourea (f) Quaternary ammonium salts: N-benzylpyridinium p-toluenesulfonate, 1-p-[N,N-bis(2-chloroethyl-)amino]benzylpyridium-p-toluenesulfonate, (g) acetylenes: diethyl acetylenedicarboxylate, methyl acetylenecarboxylate, cyanoacetylene, The reaction is preferably carried out in a solvent such as esters (e.g. ethyl acetate), ethers (e.g. diethyl ether, dioxane, tetrahydrofuran), halogenated hydrocarbons (e.g. dichloromethane, chloroform), nitriles (e.g. acetonitrile, propionitrile), aromatic hydrocarbons (e.g. benzene, toluene), pyridine, dimethylformamide, dimethyl sulfonate, sulfolane, etc. or a suitable mixture of such solvents.

The reaction may be conducted normally at a suitable temperature between about $-20°$ C. and the reflux temperature of the reaction system.

The reaction is normally carried out in the presence of a base. The base is exemplified by alkali metal hydroxides (e.g. sodium carbonate, potassium carbonate), tertiary amines (e.g. triethylamine, pyridine, α-, β- or γ-picoline, 2,6-lutidine, 4-dimethylaminopyridine, 4-pyrrolidinopyridine, dimethylaniline, diethylaniline, N-methylmorpholine, N-methylpyrolidine).

In some cases the reaction is preferably conducted in a binary system of water and an organic solvent in the presence of, what is called, a phase transfer catalyst (e.g. tetraethylammonium hydroxide, benzyltrimethylammonium bromide, benzyltriethylammonium iodide, cetyltrimethylammonium chloride or bromide).

The preferred organic solvent for the reaction is exemplified by halogenated hydrocarbons, aromatic hydrocarbons, etc., while an aqueous solution of alkali metal hydroxide is preferably used as the aqueous phase.

The alkylating agent may be used in an amount of about 1 to 100 molar equivalents, preferably 1 to 30 molar equivalents per mole of 20-demethoxy-20-hydroxymaytansinoid compound. The base may be used in a proportion of 1 to 150 molar equivalents, preferably 1 to 50 molar equivalents, and the phase transfer catalyst in an amount of 0.1 to 10 molar equivalents, preferably 1 to 5 molar equivalents.

When a bromide or chloride is used as said alkylating agent, the reaction time may in some cases be decreased by the addition of an alkali metal iodide (e.g. sodium iodide, potassium iodide), the amount of which used may range from 0.1 to 2 molecular equivalents based on the alkylating agent.

Instead of using O-alkylisourea as the alkylating agent, use may be made of the corresponding alkanol and dicyclohexylcarbodiimide.

When it is desired to obtain a compound having substituents liable to be alkylated (e.g. hydroxyl, mercapto, amino, carboxyl group) in said alkyl group, one may take the procedure of preparing a compound having such a group protected in the conventional manner and, then, subjecting the protected compound to deprotection.

As protective groups for such hydroxyl, mercapto and amino group, there may be mentioned, for example, $C_{1-4}$ alkanoyl (e.g. formyl, acetyl), $C_{2-5}$ alkoxycarbonyl (e.g. methoxycarbonyl, tert-butoxycarbonyl), benzyloxycarbonyl, helogenated $C_{1-4}$ alkanoyl (e.g. trifluoroacetyl, chloroacetyl, dichloroacetyl, bromoacetyl), etc. The protected carboxyl group includes, for example, the corresponding $C_{1-4}$ alkyl ester, benzyl ester, aryl ester (e.g. phenyl ester), and other groups.

Removal of such protective groups can be accomplished by methods known per se (e.g. reduction, acid decomposition, hydrolysis).

Further, the compound (I) wherein $R^2$ is, for example, 5-(pyrazolon-3-yl)methyl, 5-methylpyrazolyl-3-methyl or 5-(isoxazolon-3-yl)methyl (or any of their tautomeric forms produced by the shift of a hydrogen atom) or 2-(isonicotinylhydrazono)-2-phenylethyl can also be obtained by reacting hydrazine with the compound in which $R^2$ is 3-methoxycarbonyl-2-oxopropyl, hydrazine with the compound in which $R^2$ is 2,4-dioxopentyl, hydroxylamine with the compound in which $R^2$ is 3-methoxycarbonyl-2-oxopropyl and isonicotinyl hydrazide with the compound in which $R^2$ is phenacyl, respectively.

The above reaction is preferably conducted in a water-miscible solvent such as alcohol (e.g. methanol, ethanol, isopropanol), tetrahydrofuran, dioxane, acetonitrile, dimethylformamide, dimethylsulfoxide or the like or in a mixture of water and such a solvent.

The reagent (hydrazine, hydroxylamine, etc.) may be added to the reaction mixture in the form of a free base or an appropriate salt, and when the salt is employed, it is desirable that a sufficient amount of a base (e.g. alkali hydroxide, triethylamine) to yield a substantial amount of the free base if concomitantly present in the reaction system. The above-mentioned reagent may be used in an amount of 1 to 30 molar equivalents, preferably 1 to 15 molar equivalents, to the compound (II). The reaction may be conducted at a suitable temperature from the one under ice-cooling to the boiling point of the reaction system.

The compound (I) in which $R^2$ is a group having a sulfinyl or sulfonyl group, can also be produced by oxidizing a compound (I) in which $R^2$ is a group having the corresponding thioether group with a suitable oxidizing agent such as hydrogen peroxide, a peroxy acid (e.g. peracetic acid, pertrifluoroacetic acid, perbenzoic acid, m-chloroperbenzoic acid), a periodate (e.g. sodium salt), a permanganate (e.g. sodium salt, potassium salt) or the like. Furthermore, the compound (I) in which, for example, $R^2$ is a p-aminobenzyl can be produced by reducing the corresponding nitro compound by the methods known per se, and the amino compound thus obtained can be further derived to corresponding alkyl sulfonyl amino, alkylamino or dialkylamino compound by the methods known per se.

The maytansinoid compound (I) produced in the described manner can be isolated and recovered from the reaction mixture by conventional procedures, e.g. concentration, solvent extraction, chromatography, recrystallization, etc.

The maytansinoid compound (I) according to this invention has potent antimitotic activity and antitumor activities with comparatively low toxicity, and when administered to animals innocurated with tumor cells (e.g. leukemia (P-388, mouse), melanoma (B-16, mouse)), produces a marked increase in survival time. Therefore, the compound (I) can be used as an effective antitumor drug for warm-blooded animals (e.g. mouse, rat, rabbit, dog, cat, man). The compound (I) is safely administered orally or parenterally in the form of a suitable pharmaceutical preparation (e.g. injection) as formulated with a per se known carrier, diluent or the like. When the compound (I) is administered by injection, it may be given subcutaneously, intraperitoneally, intravenously and intramuscularly. When administered intravenously to melanoma, the dosage may be selected from the range of about 1 to 500 μg/kg body weight per injection, preferably 5 to 100 μg/kg body weight due to the condition, species and other factors of the animal.

The injectable preparation may be prepared in the established manner, for example by dissolving about 50 μg to 3 mg of compound (I) in about 0.5 ml of alcohol (e.g. ethanol) and making it up to 10 ml with physiological saline. When a small dosage is indicated, the above solution may be further diluted with physiological saline.

The maytansinoid compounds (I) of this invention are useful in that they display antimicrobial activity, e.g. antifungal and antiprotozoal activities. Thus, for example, the maytansinoid compounds (I) are useful for treating *Tetrahymena pyriformis* W. As an antifungal or/and antiprotozoal agent, compound (I) can be advantageously used for the investigation of bacterial flora in soil, active sludge, animal body fluids, etc. Thus, in separating useful baceteria from soil samples or in studying the action of bacteria to the exclusion of protozoa and fungi in connection with the operation and analysis of active sludge systems for waste water treatment, it is possible to ensure a selective growth of bacterial flora, not permitting growth of the concomitant fungi and protozoa. More specifically, a test sample is added to a liquid or solid medium and 0.1 ml of a 1% methanol-water solution of about 10 to 100 μg/ml of compound (I) is added to the medium, followed by incubation.

The maytansinoid compound (I), in an amount of 0.02 ml of a 1 mg/ml aqueous solution, inhibits growth of, for example, the causative microorganisms of stem rot, Helminthosporium leaf spot and sheath blight in rice plants and, therefore, can be used in the control of such plant diseases by spraying rice plants with a solution of compound (I) in 1% methanol-water, the concentration of which may range from about 0.5 to 5 μg/ml.

The starting compound (II) used for the production of the contemplated compound of this invention can be produced for example in accordance with the description in the specification of Japanese Patent Application No. 160787/1978, which was laid open on June 27, 1980 as No. 85592/1980 (United States Patent Application Ser. No. 19,612, filed on March 12, 1979 EP Publication No. 4466) on Oct. 3, 1979, i.e. by contacting a maytansinoid compound of the formula:

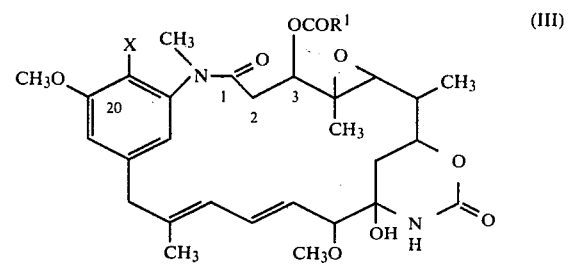

wherein X and $R^1$ are as previously defined, with a culture broth, inclusive of processed matters derived therefrom, of a microorganism belonging to the genus Bacillus, the genus Streptomyces or the genus Actinomyces, which is capable of transforming the 20-methoxy group of (III) into a hydroxyl group.

The microorganisms thus useful for the method of transforming the 20-methoxy group into a hydroxyl group include strains of the genera Bacillus, Streptomyces and Actinomyces, and their mutants, which are capable of transforming the methoxy group in 20-position of maytansinoid compound (III) into a hydroxyl group. Among the microorganisms useful for the purpose are *Bacillus megaterium* IFO 12108, *Streptomyces flavotricini* IFO 12770, *Streptomyces platensis* IFO 12901, *Streptomyces libani* IFO 13452 and *Actinomyces nigrescens* IFO 12894. The microorganisms given IFO numbers above have been listed on the List of Cultures, 1978 Sixth Edition, published by Institute for Fermentation, Osaka. The microorganisms listed there are available from the same Institute.

The compound of the above formula (III) in which X is a hydrogen atom, i.e., dechloromaytansinoid compound, can be produced for example in accordance with the description in the specification of Japanese Patent Application No. 13995/1978, which was laid open on May 20, 1980 as No. 66586/1980 (United States Patent Application Ser. No. 92,954, filed on Nov. 9, 1979, which was issued as U.S. Pat. No. 4, 256,746 on Mar. 17, 1981 EP Publication 11277 on May 28, 1980), i.e. by acylating dechloromaytansinol of the formula:

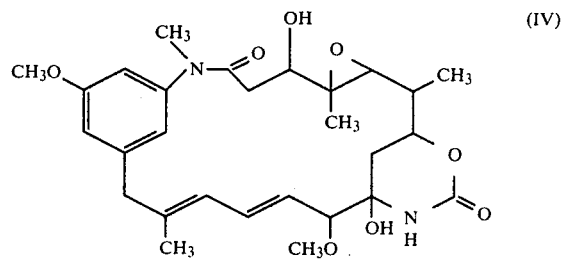

with a carboxylic acid of the formula:

R¹—COOH          (V)

wherein R¹ is as previously defined, or a reactive derivative thereof. The dechloromaytansinol (IV) can be produced by reducing a compound (III) in which X is Cl with a metal hydride (e.g. lithium aluminum hydride).

This invention will hereinafter be described in further detail by way of reference and working examples which, however, are merely illustrative and not limitative of the invention. In the reference and working examples, Rf values are those found on silical gel TLC (Merck, HPTLC) unless otherwise indicated. Further, Ansamitocin P-2, P-3 and P-4 mean the compounds (III) in which X is Cl and R¹ means ethyl, isopropyl and isobutyl, respectively. PDM-3 is a compound (II) in which X is Cl and R¹ is isopropyl, i.e. 20-demethoxy-20-hydroxymaytansinol 3-isobutyrate. Dechloro-PDM-3 means a compound (II) in which X is H and R¹ is isopropyl, i.e. 19-dechloro-20-demethoxy-20-hydroxymaytansinol 3-isobutyrate.

Reference Example 1

In 800 ml of anhydrous THF is dissolved 15.0 g of antibiotic Ansamytocin mixture (Ansamitocin P-2, 12%; Ansamitocin P-3, 71%; Ansamitocin P-4, 17%) and the solution is cooled to $-50°$ C. on a Dry Ice-ethanol bath in a dry nitrogen gas stream. Then, 13.0 g of lithium aluminum hydride (LAH) is added in one dose, and the mixture is stirred at the temperatures from $-50°$ to $-22°$ C. for 2 hours. Then, the mixture is chilled to $-28°$ C. and to this 3 g of LAH is further added. The mixture is further stirred at $-28°$ to $-22°$ C. for one hour and then rechilled to $-50°$ C. Then, 750 ml of 2N-hydrochloric acid is added dropwise with caution over a period of 30 minutes. The reaction mixture is extracted 3 times with 2.6 l, 1.6 l and 0.8 l portions of ethyl acetate and the extracts are combined, washed with a saturated aqueous solution of sodium chloride (100 ml×2) and dried (MgSO₄, 250 g). The solvent is distilled off under reduced pressure and the residue (13.6 g) is chromatographed on a column of silica gel (1.2 kg) with ethyl acetate-water (98.5:1.5, v/v), the eluate being collected in 400-g fractions. Fractions 35 through 52 are pooled, the solvent is distilled off and the residue dried in vacuo to recover 7.25 g of maytansinol. Similarly, from fractions 53 through 68 is recovered 1.55 g of an approximately equimolar mixture of maytansinol and dechloromaytansinol. Further, fractions 69 through 86 yield 0.78 g of dechloromaytansinol. The last-mentioned product, on reprecipitation from chloroform-hexane, gives 0.71 g of dechloromaytansinol as white powder.

m.p. 174°–179° C. (decompn.)

Mass spectrum (m/e) 469, etc.

UV spectrum $(\lambda_{max}^{MeOH})$nm: 231.5, 241.5, 250.5, 277.5, 286.

Reference Example 2

In 10 ml of dry dichloromethane is dissolved 90 mg (0.170 mmol) of dechloromaytansinol followed by addition of 280 mg (1.772 mmols) of isobutyric anhydride and 44 mg (0.361 mmol) of 4-dimethylaminopyridine (DMAP). The mixture is stirred at room temperature for 1.5 hours, and then 22 mg (0.180 mmol) of DMAP is further added. The mixture is stirred at the same temperature for 17 hours. The reaction mixture is washed with 0.5 N-HCl (10 ml×2), aqueous sodium hydrogen carbonate solution (10 ml) and water (10 ml×2), and after drying, the solvent is distilled off. The residue (174 mg) is dissolved in chloroform, the solution is chromatographed on a silica-gel column (20 mm out.-dia.×400 mm) with chloroform-ethanol (from 100/1 to 40/1), the eluate being collected in 25-g fractions. Fractions 42 through 65 are pooled and the solvent is distilled off, whereby 69 mg of dechloromaytansinol 3-isobutyrate is obtained as a crude product. This crude product is dissolved in ethyl acetate, the solution is allowed to stand, and the resulting crystals are collected by filtration. The above procedure yields 44 mg of dechloromaytansinol 3-isobutyrate as white prisms.

m.p. 250°–252° C. (decompn.)

Mass spectrum (m/e): 600, 557, 539, 524, etc.

UV-spectrum $(\lambda_{max}^{MeOH})$nm: 232.5, 241, 251, 277.5, 285.5.

Reference Example 3

*Streptomyces flavotricini* IFO 12770 is inoculated into a culture medium containing 1% dextrin, 1% glucose, 1% glycerol, 0.5% peptone, 0.5% yeast extract, 0.5% meat extract, 0.3% NaCl and 0.5% calcium carbonate (pH 7.2), and is cultivated under shaking at 28° C. for 48 hours. To 2 l portion of this culture broth is added 20 mg of Ansamytocin P-3 and the reaction is conducted under shaking at 28° C. for 48 hours. The reaction mixture is then extracted with ethyl acetate and the extract is filtered, washed with dilute hydrochloric acid, aqueous sodium hydrogen carbonate solution and water, dried and concentrated under reduced pressure. To the residue is added petroleum ether and the resultant precipitate is dissolved in a small amount of chloroform and purified by silica gel chromatography. The above procedure yields 12 mg of PDM-3 as white powder.

m.p. 165°–168° C.

Reference Example 4

By the procedure similar to that in Reference Example 3, dechloro-PDM-3 is obtained from dechloromaytansinol 3-isobutyrate. Rf=0.42 [solvent: chloroform-methanol=9:1, plate: silica-gel precoated glass plate (Merck 60 F₂₅₄)]

EXAMPLE 1

In 1.0 ml of dichloromethane is dissolved 31 mg of PDM-3. To this, 1.0 ml of water and 50 μl of 1 N-aqueous sodium hydroxide are added. Then, 16 mg of cetyltrimethylammonium chloride and 15 mg of ethyl p-toluenesulfonate are further added and the reaction mixture is stirred intensely at room temperature for 20 hours, made acidic with 100 μl of 1 N-HCl and extracted with chloroform. The solvent is distilled off and the residue is separated and purified by silica-gel column chromatography. The above procedure gives 4.8 mg of PDM-3-C₂₀-ethyl ether. Rf=0.44 (solvent: chloroform-methanol=95:5) Mass spectrum (m/e) 648(M⁺), 587(M⁺−61)

EXAMPLE 2

In 4.0 ml of tetrahydrofuran is dissolved 62 mg of PDM-3. To this, 0.2 ml of 1 N-aqueous sodium hydroxide is added. The mixture is cooled to $-10°$ to $-5°$ C., and under stirring, 47.5 mg of triethyloxonium fluoroborate is added. The mixture is stirred at $-5°$ to 0° C. for 15 minutes. To the reaction mixture are added 20 ml of tetrahydrofuran and anhydrous sodium sulfate, the solvent is distilled off under reduced pressure and the residue is separated and purified by silica gel column chromatography yielding 58 mg of PDM-3-$C_{20}$-ethyl ether. This compound showed identical Rf-value on TLC and mass spectrum with those of the product of Example 1.

EXAMPLE 3

In 3.2 ml of dichloromethane is dissolved 99.2 mg of PDM-3. To this, 3.2 ml of water and 0.24 ml of 1 N-aqueous sodium hydroxide are added. After further addition of 51 mg of cetyltrimethylammonium chloride and 80 mg of ethyl bromoacetate, the reaction mixture is stirred intensely at room temperature for 1.5 hours, neutralized with 0.24 ml of 1 N-HCl and extracted with chloroform. The solvent is distilled off under reduced pressure and the residue is separated and purified by silica gel column chromatography yielding 70 mg of PDM-3-$C_{20}$-ethoxycarbonylmethyl ether. Rf=0.54 (solvent: chloroform-methanol=95:5), mass spectrum (m/e): 706($M^+$), 688($M^+ -18$), 663($M^+ -43$), 645($M^+ -61$)

EXAMPLE 4

In a manner similar to that in Example 3, 31 mg of PDM-3-$C_{20}$-isopropyloxycarbonylmethyl ether is obtained from 124 mg of PDM-3 and 32 mg of isopropyl bromoacetate. Mass spectrum (m/e): 720($M^+$), 677($M^+ -43$), 659($M^+ -61$)

EXAMPLE 5

In a manner similar to that in Example 3, 121 mg of PDM-3-$C_{20}$-tert-butoxycarbonylmethyl ether is obtained from 124 mg of PDM-3 and 117 mg of tert-butyl bromoacetate. Mass spectrum (m/e): 673($M^+ -61$)

EXAMPLE 6

In a manner similar to that in Example 3, 128 mg of PDM-3-$C_{20}$-phenoxycarbonylmethyl ether is obtained from 124 mg of PDM-3 and 86 mg of phenyl bromoacetate. Mass spectrum (m/e): 693($M^+ -61$).

EXAMPLE 7

In a manner similar to that in Example 3, 68.5 mg of PDM-3-$C_{20}$-phenacyl ether is obtained from 62 mg of PDM-3 and 40 mg of phenacyl bromide. Mass spectrum (m/e): 738($M^+$), 677($M^+ -61$).

EXAMPLE 8

In a manner similar to that in Example 3, 43 mg of PDM-3-$C_{20}$-$\beta,\beta$-diethoxyethyl ether is obtained from 174 mg of PDM-3 and 165 mg of bromoacetal. Mass spectrum (m/e): 736($M^+$), 708($M^+ -28$), 675($M^+ -61$)

EXAMPLE 9

In a manner similar to that in Example 3, 84 mg of PDM-3-$C_{20}$-$\gamma$-ethoxycarbonylacetonyl ether is obtained from 124 mg of PDM-3 and 84 mg of ethyl $\gamma$-bromoacetoacetate. Mass spectrum (m/e): 687($M^+ -16$)

EXAMPLE 10

In a manner similar to that in Example 3, 64 mg of PDM-3-$C_{20}$-benzyl ether is obtained from 62 mg of PDM-3 and 34 mg of benzyl bromide. Mass spectrum (m/e): 710($M^+$), 667($M^+ -43$), 649($M^+ -61$)

EXAMPLE 11

In a manner similar to that in Example 3, 53 mg of PDM-3-$C_{20}$-acetonyl ether is obtained from 124 mg of PDM-3 and 56 mg of chloroacetone. Mass spectrum (m/e): 676($M^+$), 633($M^+ -43$), 615($M^+ -61$)

EXAMPLE 12

In 10 ml of methanol is dissolved 76 mg of PDM-3-$C_{20}$-phenoxycarbonylmethyl ether obtained in Example 6, and to this, under stirring at room temperature 0.1 ml of 1 N-aqueous sodium hydroxide solution is added. After 30 minutes, 0.1 ml of 1 N-NaOH is further added and still after 30 minutes, 0.1 ml of 1 N-NaOH is added (total 0.3 ml). After addition of the total amount of 1 N-NaOH, the mixture is allowed to stand for 15 minutes, then neutralized with 0.3 ml of 1 N-HCl and concentrated to dryness under reduced pressure. The residue is purified by silica gel chromatography to obtain 68 mg of PDM-3-$C_{20}$-carboxymethyl ether. Rf=0.31 (solvent: acetonitrile-water=95:5). Mass spectrum (m/e): 617($M^+ -61$)

EXAMPLE 13

In 1.0 ml of methanol is dissolved 38 mg of PDM-3-$C_{20}$-$\gamma$-ethoxycarbonylacetonyl ether obtained in Example 9, and to this, under stirring at room temperature, 5 mg of hydrazine hydrate is added. After 30 minutes, 5 mg of hydrazine hydrate is further added and the mixture is allowed to stand for an hour. The solvent is concentrated to dryness under reduced pressure and the residue is separated purified by silica gel column chromatography yielding 18 mg of PDM-3-$C_{20}$-(5-pyrazolon-3-yl)methyl ether. Rf=0.11 (solvent:chloroform-methanol=95:5); mass spectrum (m/e): 655($M^+ -61$)

EXAMPLE 14

In a manner similar to that in Example 3, 60 mg of PDM-3-$C_{20}$-pivaloyloxymethyl ether is obtained from 124 mg of PDM-3 and 120 mg of chloromethyl pivalate. Mass spectrum (m/e): 673($M^+ -61$)

EXAMPLE 15

In a manner similar to that in Example 2, 53 mg of dechloro-PDM-3-$C_{20}$-ethyl ether is obtained from 59.2 mg of dechloro-PDM-3, 0.2 ml of 1 N-aqueous sodium hydroxide solution and 51 mg of triethyloxonium fluoroborate. Mass spectrum (m/e): 614($M^+$), 553($M^+ -61$).

EXAMPLE 16

In 5 ml of anhydrous dichloromethane are dissolved 105.8 mg of PDM-3, 123 mg of allyl bromide and 124 mg of cetyltrimethylammonium bromide and to this, 10.2 ml of 0.1 N-aqueous sodium hydroxide is added. The mixture is stirred at room temperature for 2 hours, and then neutralized with 1 N-HCl. To this solution is added a saturated aqueous solution of sodium chloride and the organic layer is taken out, washed with aqueous sodium chloride and dried ($Na_2SO_4$). The solvent is distilled off, the residue dissolved in ethyl acetate and the insolubles are filtered off. The filtrate is concentrated and the residue chromatographed on silica gel ($SiO_2$ approx. 40 g; solvent: ethyl acetate, approx. 50 ml, and, then, ethyl acetate-ethyl acetate saturated with water=4:1, v/v), the eluate being collected in 17-g fractions. Fractions 9 through 16 are combined and the solvent is distilled off, yielding 50.5 mg of PDM-3-$C_{20}$-allyl ether. Mass spectrum (m/e): 599(M+ −61)

EXAMPLE 17

In a manner similar to that in Example 16, 106 mg of PDM-3, 122 mg of propargyl bromide, 10.3 ml of 0.1 N-NaOH and 124.5 mg of cetyltrimethylammonium bromide are reacted at room temperature for 3 hours and the reaction mixture is worked up and chromatographed as in Example 16, yielding 41.7 mg of PDM-3-$C_{20}$-propargyl ether. Mass spectrum (m/e): 597(M+ −61).

EXAMPLE 18

In a manner similar to that in Example 16, a mixture of 94.2 mg of PDM-3, 50 μl of chloroacetonitrile, 6.1 ml of 0.1 N-NaOH and 110.4 mg of cetyltrimethylammonium bromide is stirred at room temperature overnight. Then, 25 μl of chloroacetonitrile and 4.0 ml of 0.1 N-NaOH are further added, and stirring is continued for 7 hours. Thereafter, the reaction mixture is worked up in the same manner as in Example 16. The residue is subjected to silica gel chromatography ($SiO_2$, 44 g; solvent, chloroform-methanol=20:1, v/v), the eluate being collected in 20-g fractions. Fractions 21 through 25 are combined to obtain 34.3 mg of PDM-3-$C_{20}$-cyanomethyl ether. Mass spectrum (m/e): 598(M+ −61).

EXAMPLE 19

In 3 ml of anhydrous dichloromethane is dissolved 82.8 mg of PDM-3. To this are added 100 μl of chloromethyl methyl sulfide and 100 μl of triethylamine. The mixture is stirred at room temperature for 5 hours, and then the solvent is distilled off. The residue is dissolved in ethyl acetate, washed with aqueous sodium chloride solution and dried. The solvent is then distilled off and the residue is chromatographed on silica gel (solvent: ethyl acetate) as in Example 3, yielding 25.3 mg of PDM-3-$C_{20}$-methylthiomethyl ether. Mass spectrum (m/e): 619(M+ −61).

EXAMPLE 20

In a manner similar to that in Example 3, 72 mg of PDM-3-$C_{20}$-diacetylmethyl ether is obtained from 124 mg of PDM-3 and 72 mg of 3-bromoacetylacetone. Mass spectrum (m/e): 657(M+ −61).

EXAMPLE 21

In a manner similar to that in Example 3, 56 mg of PDM-3-$C_{20}$-γ-acetylacetonyl ether is obtained from 128 mg of PDM-3 and 286 mg of 1-bromoacetylacetone. Mass spectrum (m/e): 657(M+ −61).

EXAMPLE 22

In a manner similar to that in Example 3, 46 mg of PDM-3-$C_{20}$-p-chlorobenzyl ether is obtained from 124 mg of PDM-3 and 161 mg of p-chlorobenzyl chloride. Mass spectrum (m/e): 744(M+), 683(M+ −61).

EXAMPLE 23

In a manner similar to that in Example 3, 142 mg of PDM-3-$C_{20}$-p-chlorophenacyl ether is obtained from 124 mg of PDM-3 and 234 mg of p-chlorophenacyl bromide. Mass spectrum (m/e): 772(M+), 711(M+ −61).

EXAMPLE 24

In a manner similar to that in Example 3, 281 mg of PDM-3-$C_{20}$-p-nitrobenzyl ether is obtained from 248 mg of PDM-3 and 432 mg of p-nitrobenzyl bromide. Mass spectrum (m/e): 694(M+ −61).

EXAMPLE 25

In a manner similar to that in Example 3, 57 mg of PDM-3-$C_{20}$-(3,4,5-trimethoxy)benzyl ether is obtained from 124 mg of PDM-3 and 217 mg of 3,4,5-trimethoxybenzyl chloride. Mass spectrum (m/e): 739(M+ −61).

EXAMPLE 26

In a manner similar to that in Example 3, 13 mg of PDM-3-$C_{20}$-(3,4-dimethoxy)benzyl ether is obtained from 124 mg of PDM-3 and 187 mg of 3,4-dimethoxybenzyl chloride. Mass spectrum (m/e): 709(M+ −61).

EXAMPLE 27

In a manner similar to that in Example 3, 127 mg of PDM-3-$C_{20}$-p-cyanobenzyl ether is obtained from 124 mg of PDM-3 and 196 mg of p-cyanobenzyl bromide. Mass spectrum (m/e): 674(M+ −61).

EXAMPLE 28

In a manner similar to that in Example 3, 62 mg of PDM-3-$C_{20}$-p-acetoxybenzyl ether is obtained from 124 mg of PDM-3 and 229 mg of p-acetoxybenzyl bromide. Mass spectrum (m/e): 768(M+), 707(M+ −61).

EXAMPLE 29

In a manner similar to that in Example 1, 18 mg of PDM-3-$C_{20}$-2-(2-ethoxyethoxy)ethyl ether is obtained from 124 mg of PDM-3 and 288 mg of 2-(2-ethoxyethoxy)ethyl p-toluenesulfonate. Mass spectrum (m/e): 736(M+), 675(M+ −61).

EXAMPLE 30

In a manner similar to that in Example 3, 12 mg of PDM-3-$C_{20}$-(7-bromo-2,6-dioxo)heptyl ether is obtained from 124 mg of PDM-3 and 29 mg of 1,7-dibromo-2,6-heptanedione. Mass spectrum (m/e): 764(M+ −61).

EXAMPLE 31

In a manner similar to that in Example 1, 23 mg of PDM-3-$C_{20}$-hexaethyleneglycolyl ether is obtained from 124 mg of PDM-3 and 436 mg of hexaethylene glycol p-toluenesulfonate. Mass spectrum (m/e): 823(M+ −61).

EXAMPLE 32

PDM-3-$C_{20}$-p-nitrobenzyl ether obtained in Example 24 (151 mg) is dissolved in 12 ml of methanol. To this solution, 3 ml of water and a solution of 45 mg of calcium chloride in 0.5 ml of water are added successively. To this, 150 mg of zinc powder is added and the mixture is stirred at 60° C. for one hour, and then allowed to cool. The insolubles are filtered off and the filtrate is concentrated. The residue is extracted with chloroform and the extract dried over anhydrous $Na_2SO_4$. The solvent is evaporated under reduced pressure to give 141 mg of PDM-3-$C_{20}$-p-aminobenzyl ether. Mass spectrum (m/e): 664(M+ −61), 559(M+ −166).

EXAMPLE 33

PDM-3-$C_{20}$-p-aminobenzyl ether (36.3 mg) obtained in Example 32 is dissolved in 5.0 ml of dry dichloromethane. To this, 160 mg of dry pyridine and 115 mg of methanesulfonic chloride are added with stirring at room temperature. After three hour's standing, 15 ml of chloroform and 15 ml of water are added to the reaction mixture and the organic phase is separated. The aqueous layer is extracted twice with 15 ml each of chloroform. The combined extracts are dried over anhydrous $Na_2SO_4$. The solvent is evaporated under reduced pressure and the residue purified by the silica-gel chromatography giving 27 mg of PDM-3-$C_{20}$-p-methanesulfonamidobenzyl ether. Mass spectrum (m/e): 742($M^+$ −61).

EXAMPLE 34

PDM-3-$C_{20}$-p-acetoxybenzyl ether (27 mg) obtained in Example 28 is dissolved in 5.4 ml of methanol. To this, under stirring at room temperature, 0.54 ml of triethylamine is added. After three hours, the solvent is evaporated off under reduced pressure and the residue is purified by the silica-gel chromatographic technique giving 23 mg of PDM-3-$C_{20}$-p-hydroxybenzyl ether. Mass spectrum (m/e): 665($M^+$ −61).

EXAMPLE 35

PDM-3 (171 mg) is dissolved in 5 ml of dichloromethane. To this 70 μl of methyl acetylenecarboxylate and 15 μl of N-methylmorpholine are added and the mixture is stirred at room temperature for three hours. The reaction mixture is washed with 0.1 N HCl and the organic phase separated. The aqueous layer is extracted with chloroform and the combined extracts are washed with water and dried ($Na_2SO_4$). The solvent is evaporated and the residue is purified by the silica-gel chromatographic technique, giving 48 mg of PDM-3-$C_{20}$-(E)-(2-methoxycarbonyl)vinyl ether (Fraction 1; eluated first) and 27 mg of PDM-3-$C_{20}$-(Z)-(2-methoxycarbonyl)vinyl ether (Fraction 2; eluated secondly). Fraction 1 (E-isomer): Rf=0.76 (Solvent: ethyl acetate saturated with water). NMR (90 MHz, in $CDCl_3$) δ 7.75 (1H, d, J=12 Hz), 5.58(1H, d, J=12 Hz). Mass spectrum (m/e): 704($M^+$), 643($M^+$ −61). Fraction 2 (Z-isomer): Rf=0.70 (Solvent: as above). NMR (90 MHz, in $CDCl_3$) 6.77(1H,d,J=6.1 Hz), 5.30(1H,d,J=6.1 Hz). Mass Spectrum (m/e): 704($M^+$), 643($M^+$ −61).

EXAMPLE 36

PDM-3 (31 mg) is dissolved in 3 ml of dichloromethane. To this, 30 μl of diethyl acetylenecarboxylate and 15 mg of 4-dimethylaminopyridine are added and the mixture is stirred at room temperature overnight. Then, the reaction mixture is concentrated and the residue subjected to a silica-gel chromatography to give, as in Example 35, two products: Fraction 1 (3.4 mg) and Fraction 2 (2 mg). These products are the geometric isomers of PDM-3-$C_{20}$-(1,2-diethoxycarbonyl)vinyl ether. Fraction 1: Rf=0.83 (Solvent: ethyl acetate saturated with water). Mass spectrum (m/e): 729($M^+$ −61). Fraction 2: Rf=0.76 (Solvent: as above). Mass spectrum (m/e): 729($M^+$ −61).

EXAMPLE 37

To a solution of PDM-3 (97 mg) in 5 ml of dichloromethane, 32 μl of cyanoacetylene and 5 μl of N-methylmorpholine are added and the mixture is stirred at room temperature for 30 minutes. The reaction mixture is evaporated to dryness under reduced pressure and the residue is dissolved in ethyl acetate. The solution is washed with 0.5 N HCl and then with aqueous NaCl solution. The solvent is evaporated off and the residue is chromatographed on a silica gel (40 g) column with EtOAc/EtOAc saturated with water=3/1(v/v), collecting the eluate in 17-g fractions. Fractions 9–11 are combined and the solvent is evaporated giving 39 mg of PDM-3-$C_{20}$-(E)-β-cyanovinyl ether (Compound A) and similarly, from fractions 14–25, 37 mg of PDM-3-$C_{20}$-(Z)-β-cyanovinyl ether (Compound B) is obtained, Compound A: Mass spectrum (m/e): 610($M^+$ −61). NMR (in $CDCl_3$) 5.14 and 7.46 (each 1H, d, J=13 Hz), etc. Compound B: Mass spectrum: 610 ($M^+$ −61). NMR(in $CDCl_3$) 5.25 and 7.61 (each 1H, d, J=7 Hz), etc.

EXAMPLE 38

In a manner similar to that in Example 3, 87 mg of PDM-3-$C_{20}$-α-naphthylmethyl ether is obtained from 124 mg of PDM-3 and 177 mg of α-chloromethylnaphthalene. Mass spectrum (m/e): 760($M^+$), 699($M^+$ −61).

EXAMPLE 39

In a manner similar to that in Example 3, 116 mg of PDM-3-$C_{20}$-β-naphthylmethyl ether is obtained from 124 mg of PDM-3 and 221 mg of β-bromomethylnaphthalene. Mass spectrum (m/e): 760($M^+$), 699($M^+$ −61).

EXAMPLE 40

PDM-3-$C_{20}$-phenacyl ether obtained in Example 7 (20 mg) is dissolved in 2.7 ml of methanol. To this, 37 mg of isonicotinic acid hydrazine and 22 mg of sodium acetate are added and the mixture is stirred for three days at 60° C. The solvent is evaporated under reduced pressure and the chloroform-soluble portion of the residue subjected to a silica-gel (10 g) chromatography (Solvent: methanol/chloroform=5/95 (v/v) giving 8 mg of PDM-3-$C_{20}$-(2-isonicotinoylhydrazono-2-phenyl)ethyl ether. Mass spectrum (m/e): 857($M^+$).

EXAMPLE 41

In a manner similar to that in Example 1, 38 mg of PDM-3-$C_{20}$-p-[N,N-bis(2-chloroethyl)amino]benzyl ether is obtained from 124 mg of PDM-3 and 192 mg of 1- p-[N,N-bis(2-chloroethyl)amino]benzyl pyridinium p-toluenesulfonate. Mass spectrum (m/e): 849($M^+$); 788($M^+$ −61).

EXAMPLES OF Pharmaceutical Compositions

| Example A | | |
|---|---|---|
| Composition for Injection | | |
| (1) | $C_{20}$-Phenacyl ether of 20-demethoxy-20-hydroxymaytansinol-3-isobutyrate | 100 mg |
| (2) | Ethanol | 10 g |
| (3) | Polysorbate 80 (Tween 80) | 40 g |
| (4) | Mannitol | 20 g |
| (5) | Distilled water, a sufficient quantity to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

Experimental Data

Antitumor Activity

Therapeutic tests were carried out in mice according to NCI-protocol 1,300, Cancer Chemother, Reports, Part 3, 1972, Vol. 3, No. 2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C %) |
|---|---|---|
| $C_{20}$-Phenacylether of 20-demethoxy-20-hydroxy-maytansinol-3-isobutyrate (PDM-3-$C_{20}$-phenacylether) | 400 | 203 |
| | 200 | 211 |
| | 100 | 176 |
| | 50 | 188 |
| $C_{20}$-($\beta,\beta$-Diethoxy)ethyl ether of 20-demethoxy-20-hydroxymaytansinol-3-isobutyrate (PDM-3-$C_{20}$-($\beta,\beta$-diethoxy)ethyl ether) | 100 | 240 |
| | 50 | 211 |
| | 25 | 194 |
| $C_{20}$Benzylether of 20-demethoxy-20-hydroxy-maytansinol-3-isobutyrate (PDM-3-$C_{20}$-benzylether) | 100 | 234 |
| | 50 | 220 |
| | 25 | 182 |

Antiprotozoal activity

Antiprotozoal activity of compound (I) was assayed with Tetrahymena pyriformis W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The microorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC (μg/ml) Tetrahymena pyriformis W |
|---|---|
| $C_{20}$-ethoxy ether | ≦1 |
| $C_{20}$-ethoxycarbonylmethyl ether | 1-2 |
| $C_{20}$-γ-ethoxycarbonylacetonyl ether | 4 |
| $C_{20}$-benzyl ether | ≦1 |
| $C_{20}$-2-isonicotinoylhydrazono-2-phenylethyl ether | 2-4 |
| $C_{20}$-allyl ether | ≦1 |
| $C_{20}$-methoxycarbonylvinyl | ≦1 |
| $C_{20}$-2-(2-ethoxyethoxy)ethyl ether | 2 |

What is claimed is:

1. A compound of the formula:

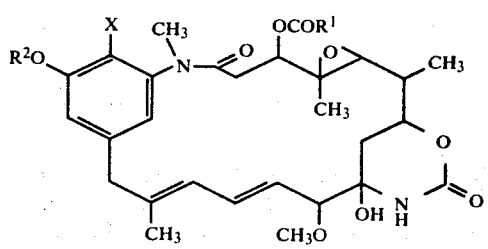

wherein

X is hydrogen or chlorine, $R^1$ is $C_{2-4}$alkyl $R^2$ is $C_{1-5}$alkyl substituted with oxo, $C_{2-5}$alkoxycarbonyl, or/and phenyl.

2. A compound according to claim 1, wherein X is chlorine.

3. A compound according to claim 1, wherein $R^1$ is isopropyl.

4. A compound according to claim 1, wherein $R^2$ is methyl attached to a phenyl group which is substituted with $C_{1-4}$ alkyl, hydroxyl, $C_{1-4}$-alkoxy, $C_{1-4}$-alkanoyloxy, $C_{2-5}$-alkoxycarbonyl, halogen, nitro, cyano, trifluoromethyl, amino, mono-$C_{1-4}$-alkylamino, di-$C_{1-4}$-alkylamino, or/and sulfinylamino.

5. A compound according to claim 1, wherein $R^2$ is $C_{2-5}$ alkyl substituted with oxo, $C_{2-5}$ alkoxycarbonyl or/and unsubstituted phenyl.

6. A compound according to claim 4, wherein the substituted phenyl is anilino or bis(2-chloroethyl)aminophenyl.

7. A compound according to claim 1, said compound being $C_{20}$-phenacyl ether of 20-demethoxy-20-hydroxymaytansinol 3-isobutylate.

8. A compound according to claim 1, said compound being $C_{20}$-γ-ethoxycarbonylacetonyl ether of 20-demethoxy-20-hydroxymaytansinol 3-isobutylate.

9. A compound according to claim 1, said compound being $C_{20}$-p-aminobenzyl ether of 20-demethoxy-20-hydroxymaytansinol 3-isobutylate.

10. $C_{20}$-$\beta,\beta$-diethoxyethyl ether of 20-demethoxy-20-hydroxymaytansinol 3-isobutylate.

11. A pharmaceutical composition suitable for inhibiting the growth of tumor cells and prolonging the survival time of a tumor-bearing warm-blooded animal, which contains an amount effective for inhibiting the growth of tumor cells and prolonging the survival time of a tumor-bearing warm-blooded animal of a compound of the formula:

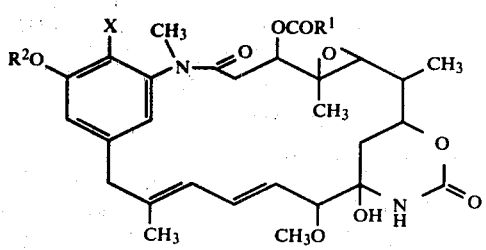

wherein

X is hydrogen or chlorine, $R^1$ is $C_{2-4}$alkyl $R^2$ is $C_{1-5}$alkyl substituted with oxo, $C_{2-5}$alkoxycarbonyl, or/and phenyl.

12. A method for inhibiting the growth of tumor cells and prolonging the survival time of a tumor-bearing warm-blooded animal, which comprises administering to said animal an amount effective for inhibiting the growth of tumor cells and prolonging the survival time of a tumor-bearing animal of a compound of the formula:

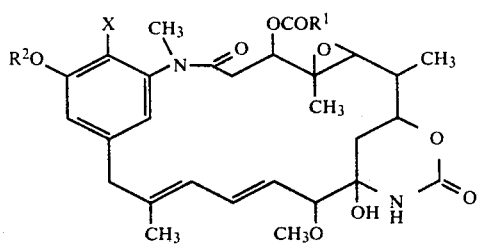
wherein
X is hydrogen or chlorine,
$R^1$ is $C_{2-4}$alkyl
$R^2$ is $C_{1-5}$alkyl substituted with oxo, $C_{2-5}$alkoxycarbonyl, or/and phenyl.
* * * * *